(12) United States Patent
Lee

(10) Patent No.: US 10,557,816 B2
(45) Date of Patent: Feb. 11, 2020

(54) SENSOR ELEMENT FOR DETECTING HCL GAS, SENSOR DEVICE HAVING THE SENSOR ELEMENT, AND METHOD OF MANUFACTURING THE SENSOR ELEMENT

(71) Applicant: Seoung Choul Lee, Daejeon (KR)

(72) Inventor: Seoung Choul Lee, Daejeon (KR)

( * ) Notice: Subject to any disclaimer, the term of this patent is extended or adjusted under 35 U.S.C. 154(b) by 94 days.

(21) Appl. No.: 15/831,820

(22) Filed: Dec. 5, 2017

(65) Prior Publication Data
US 2019/0137442 A1    May 9, 2019

(30) Foreign Application Priority Data

Nov. 3, 2017  (KR) .................. 10-2017-0146156

(51) Int. Cl.
| | |
|---|---|
| *C25D 9/04* | (2006.01) |
| *G01N 27/407* | (2006.01) |
| *G01N 33/00* | (2006.01) |
| *B32B 15/04* | (2006.01) |
| *C25D 11/00* | (2006.01) |
| *C25D 9/06* | (2006.01) |

(52) U.S. Cl.
CPC ........... *G01N 27/4074* (2013.01); *C25D 9/04* (2013.01); *C25D 9/06* (2013.01); *C25D 11/00* (2013.01); *G01N 33/0052* (2013.01)

(58) Field of Classification Search
None
See application file for complete search history.

(56) References Cited

U.S. PATENT DOCUMENTS

| | | | | | |
|---|---|---|---|---|---|
| 2,847,493 | A | * | 8/1958 | Smyth ................... | H01M 6/182 429/318 |
| 3,822,198 | A | * | 7/1974 | Bauke ................. | G01N 27/333 204/419 |
| T966,003 | I4 | * | 1/1978 | Maskasky ............ | G03C 1/4965 430/502 |

FOREIGN PATENT DOCUMENTS

KR     10-1729937 B1    5/2017

\* cited by examiner

*Primary Examiner* — Humera N Sheikh
*Assistant Examiner* — Xiaobei Wang
(74) *Attorney, Agent, or Firm* — Paratus Law Group, PLLC

(57) ABSTRACT

The present invention relates to a sensor element for detecting hydrogen chloride (HCl) gas, a sensor device having the sensor element, and a method of manufacturing the sensor element, wherein the sensor element includes: an ionic layer including a Ag ion obtained through ionization; an ion conductive layer, in which the Ag ion is conducted, the ion conductive layer being formed on the ionic layer; and a reactive layer, in which the Ag ion conducted from the ion conductive layer and HCl gas react with each other, the reactive layer being formed on the ion conductive layer. The sensor element detects HCl gas generated from insulting materials when fire occurs, thereby detecting an electrical fire and preventing gas and fire spreading.

4 Claims, 5 Drawing Sheets

SENSOR ELEMENT FOR DETECTING HCL GAS, SENSOR DEVICE HAVING THE SENSOR ELEMENT, AND METHOD OF MANUFACTURING THE SENSOR ELEMENT

CROSS REFERENCE TO RELATED APPLICATION

The present application claims priority to Korean Patent Application No. 10-2017-0146156, filed Nov. 3, 2017, the entire contents of which is incorporated herein for all purposes by this reference.

BACKGROUND OF THE INVENTION

Field of the Invention

The present invention relates generally to a sensor element for detecting hydrogen chloride (HCl) gas, a sensor device having the sensor element, and a method of manufacturing the sensor element. More particularly, the present invention relates to a sensor element for detecting HCl gas, a sensor device having the sensor element, and a method of manufacturing the sensor element, wherein the sensor element detects HCl gas generated from insulating materials when fire occurs, thereby detecting an electrical fire and preventing gas and fire spreading.

Description of the Related Art

Recently, the need for gas sensors detecting environmental hazardous gas easily is critical as concerns about hazardous gas, atmospheric environment, and human safety are increased.

A gas sensor detects types and concentration of gas by chemisorptions occurring on the surface of materials. When gas is adsorbed on the surface of such materials, electrical conductivity near the surface changes such that a gas sensor detects gas.

In particularly, specific material detection techniques are widely applied throughout industry. Among such materials, hydrogen chloride (HCl) gas is widely used in various fields. In regards to HCL gas, there are exhaust regulations according to air pollution control laws and exposure regulations according to labor laws due to environmental contamination, corrosion, and toxic characteristics of HCl gas. In addition, HCl gas essentially used in production processes of organic compounds is included in small amounts in products containing organic compounds wherein the HCL gas imparts thermal stability to such organic compounds. In addition, sheaths of electric wires and cables in electronic products are generally composed of polyethylene, intermediate material (asphalt), etc. Such sheaths release toxic gases such as HCl gas, carbon monoxide (CO), carbon dioxide ($CO_2$), and so on upon combustion.

Therefore, various studies of sensor techniques configured to detect HCl gas generated from insulating materials when fire occurs, thereby detection of an electrical fire and prevention of fire spreading are possible.

DOCUMENTS OF RELATED ART (Patent Document 1) Korean Patent No. 10-1729937, entitled "Semiconductor type HCl gas sensor and manufacturing method thereof", and registered on Apr. 19, 2017.

SUMMARY OF THE INVENTION

Accordingly, the present invention has been made keeping in mind the above problems occurring in the related art, and the present invention is intended to provide a sensor element for detecting hydrogen chloride (HCl) gas, a sensor device having the sensor element, and a method of manufacturing the sensor element, wherein the sensor element detects HCl gas generated from insulating materials when a fire occurs, thereby detecting an electrical fire and preventing gas and fire spreading.

In order to achieve the above objects, there is provided a sensor element for detecting HCl, the sensor element including: an ionic layer including a Ag ion obtained through ionization; an ion conductive layer, in which the Ag ion is conducted, the ion conductive layer being formed on the ionic layer; and a reactive layer, in which the Ag ion conducted from the ion conductive layer and HCl gas react with each other, the reactive layer being formed on the ion conductive layer.

In addition, the ion conductive layer may include AgI that is a solid electrolyte In addition, the reactive layer may include AgCl that reacts with the HCl gas.

Next, in order to achieve the above objects, there is provided a method of manufacturing a sensor element for detecting HCl, the method including: pretreating an ionic layer including a Ag ion; forming an ion conductive layer and a reactive layer on the ionic layer sequentially; and heat treating a sensor element provided with the ion conductive layer and the reactive layer formed on the ionic layer.

In addition, the forming the ion conductive layer and the reactive layer on the ionic layer sequentially may be performed by any one method or two or more methods selected from the group consisting of electroplating, depositing, and dipping.

As described above, the HCl gas detecting sensor element manufactured by using a Ag-based solid electrolyte according to an embodiment of the present invention can efficiently detect HCl gas generated from insulting materials when fire occurs, thereby detecting an electrical fire and preventing fire spreading.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
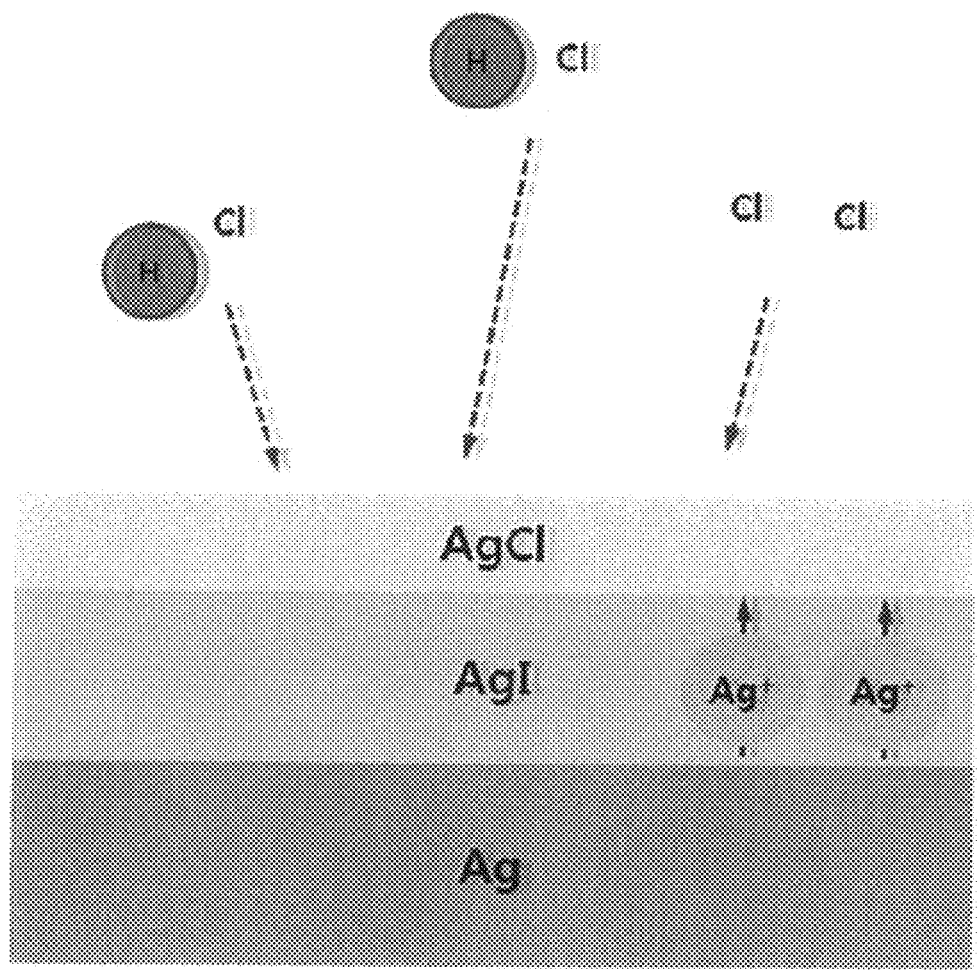
FIG. 1 is a schematic view of a sensor element for detecting HCl gas according to an embodiment of the present invention.

The exemplary embodiments according to the concept of the present invention may be variously modified and may have various shapes, so examples of which are illustrated in the accompanying drawings and will be described in detail with reference to the accompanying drawings. However, it should be understood that the exemplary embodiments according to the concept of the present invention are not limited to the embodiments which will be described hereinbelow with reference to the accompanying drawings, but various modifications, equivalents, additions and substitutions are possible, without departing from the scope and spirit of the invention.

Like reference numerals are used to identify like elements throughout different drawings. Further, in the following description, if it is decided that the detailed description of known function or configuration related to the invention makes the subject matter of the invention unclear, the detailed description is omitted.

It will be understood that, although the terms first, second, etc. may be used herein to describe various elements, these elements should not be limited by these terms. These terms are only used to distinguish one element, from another element.

For instance, a first element discussed below could be termed a second element without departing from the teachings of the present invention. Similarly, the second element could also be termed the first element.

The term "and/or" includes any and all combinations of one or more of the associated listed items.

It will be understood that when an element is referred to as being "coupled" or "connected" to another element, it can be directly coupled or connected to the other element or intervening elements may be present therebetween.

In contrast, it should be understood that when an element is referred to as being "directly coupled" or "directly connected" to another element, there are no intervening elements present. Further, the terms used herein to describe a relationship between elements, for example, "between", "directly between", "adjacent", or "directly adjacent" should be interpreted in the same manner as those described above.

The terminology used herein is for the purpose of describing particular embodiments only and is not intended to be limiting.

As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As shown in FIG. 1, the present invention relates to a sensor element for detecting HCl gas, the sensor element including: an ionic layer including a Ag ion obtained through ionization; an ion conductive layer, in which the Ag ion is conducted, the ion conductive layer being formed on the ionic layer; and a reactive layer, in which the Ag ion conducted from the ion conductive layer and HCl gas reacts with each other, the reactive layer being formed on the ion conductive layer.

In the present invention, the ionic layer may be an Ag substrate.

At this point, the ion conductive layer may include AgI that is a solid electrolyte.

Figure 2:
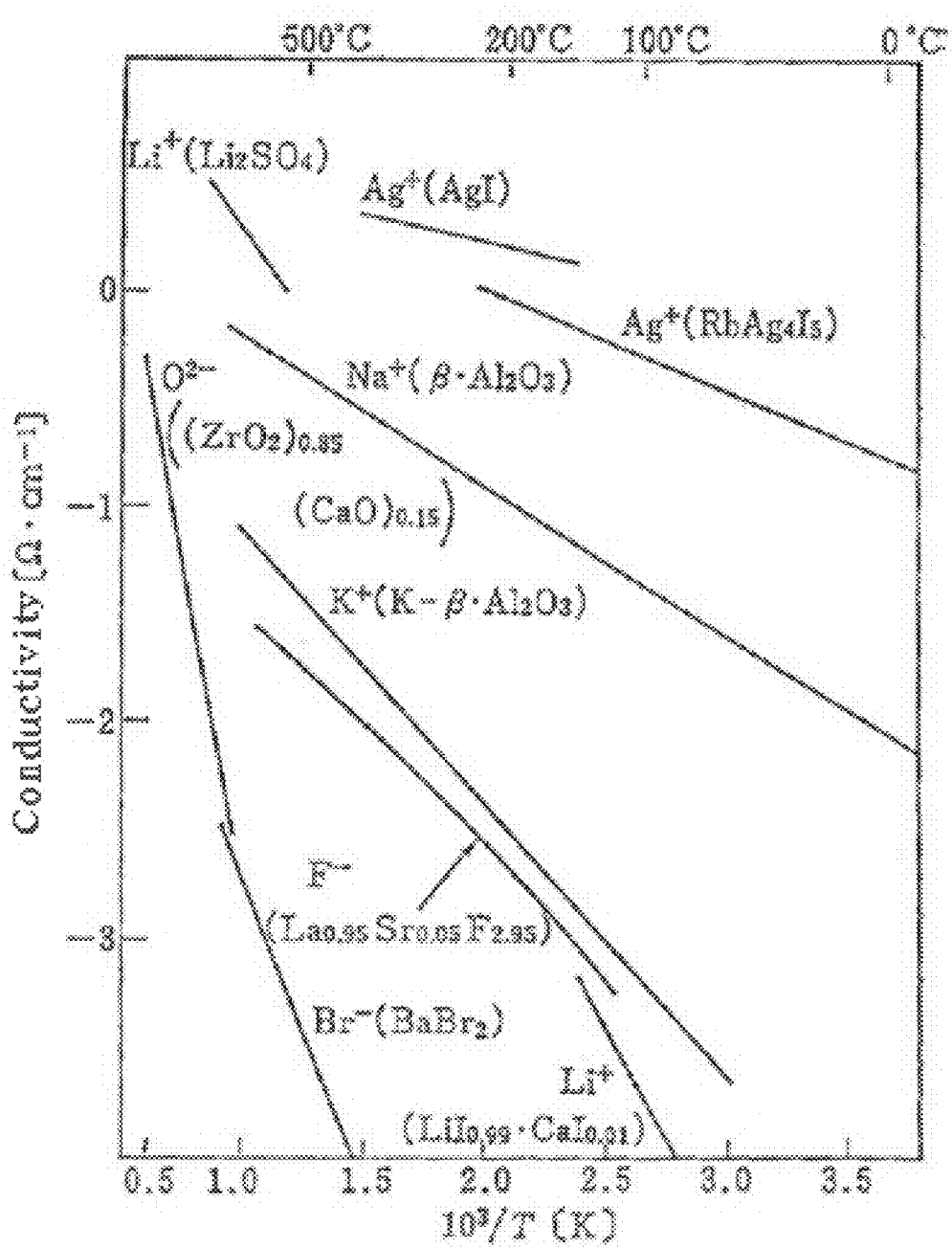
FIG. 2 is a graph showing temperature dependence of conductivities of solid electrolytes.

In case of solid electrolytes, electrical conduction is generated by the movement of ions, and such ionic conductivity can be applied to a gas sensor. In case of α-AgI, which is a solid electrolyte, the number of Ag+ ion is larger than the number of the lattice point of Ag+ ion, so Ag+ ions can move rapidly. The electrical conductivity (conductivity) of the solid electrolytes is generally lower than metals and higher than Si semiconductors. As shown in FIG. 2, the conductivity increases exponentially as a temperature increases.

The reactive layer may include AgCl that reacts with HCl gas.

The sensor element for detecting HCl gas has a structure wherein the ionic layer, the ion conductive layer, and the reactive layer are sequentially laminated and the sensor element has a characteristic that an open circuit voltage changes with an inflow of HCl gas.

Hereinafter, the operation principle of the sensor element for detecting HCl gas will be described.

The ionic layer, the Ag substrate, conducts electric current as a substrate of the sensor element and an electrode, and the ion conductive layer and the reactive layer function as a sensing material site where $Ag^+$ ion moves inside and on a surface thereof and where HCl gas is adsorbed.

In detail, in the Ag substrate, which is the ionic layer, Ag ionizes into $Ag^+$ through ionization. That is, Ag loses an electron ($e^-$) and ionizes into the form of $Ag^+$. Ionized $Ag^+$ passes the ion conductive layer and is conducted to the reactive layer. The $Ag^+$ ion conducted to the reactive layer reacts with HCl gas.

At this point, HCl gas exists as HCl gas $\leftrightarrow \frac{1}{2}H_2 + \frac{1}{2}Cl_2$ within one space. That is, HCl gas exists as HCl gas, $\frac{1}{2}H_2$, and $\frac{1}{2}Cl_2$, respectively.

Such HCl gas contacts with a surface of the reactive layer, which is AgCl. Here, $\frac{1}{2}Cl_2$ obtains $e^-$ on the surface of the reactive layer and becomes $Cl^-$. In addition, $Ag^+$ ion conducted to the reactive layer reacts with $Cl^-$ and becomes AgCl. The sensor element uses such a principle, thereby detecting existing Cl in reactant gases.

Due to such process, electromotive force is generated between the ionic layer, which is the Ag substrate, and the reactive layer, which is AgCl. That is, when HCl gas reacts with the reactive layer, which is AgCl, the electromotive force between the ionic layer, which is the Ag substrate, and the reactive layer, which is AgCl, detect HCl gas.

Figure 3:
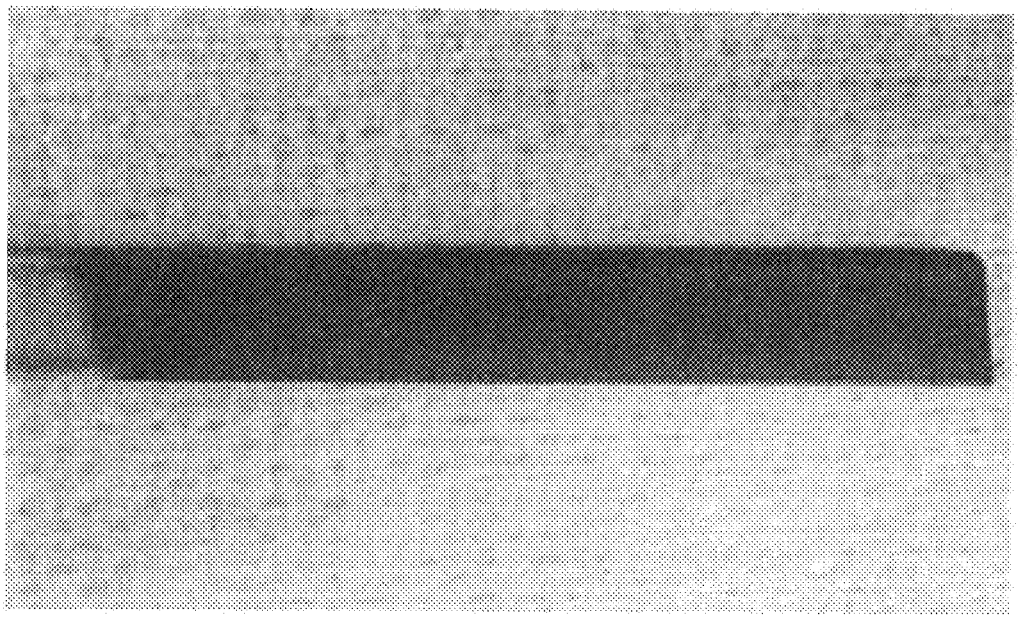
FIG. 3 is a photograph of a AgCl/AgI/Ag specimen according to an embodiment of the present invention.

FIG. 3 is a photograph of a AgCl/AgI/Ag specimen manufactured by electroplating AgI and AgCl on the Ag substrate subsequently. Such a sensor element for detecting HCl gas may be manufactured by any one method or two or more methods selected from the group consisting of electroplating, plating, depositing, and dipping. In the sensor element manufactured by the method(s), the particle size of the AgI layer ranges from 0.3 μm to 0.6 μm and the particle size of the AgCl layer ranges from 0.4 μm to 1.0 μm.

Figure 4:
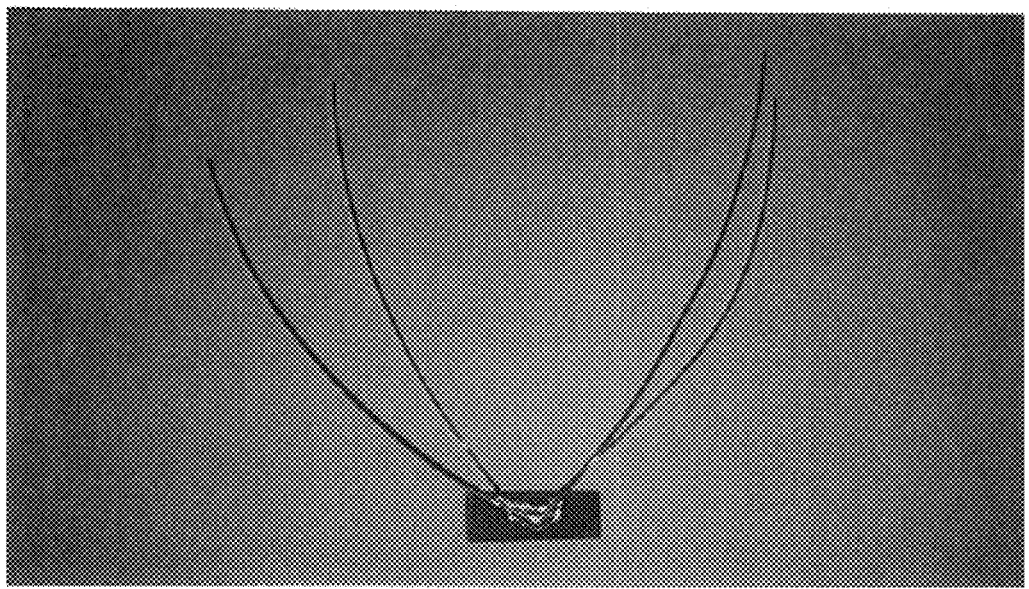
FIG. 4 is a photograph showing a plating surface of a AgCl/AgI/Ag specimen connected with Ag wires according to an embodiment of the present invention.
Figure 5:
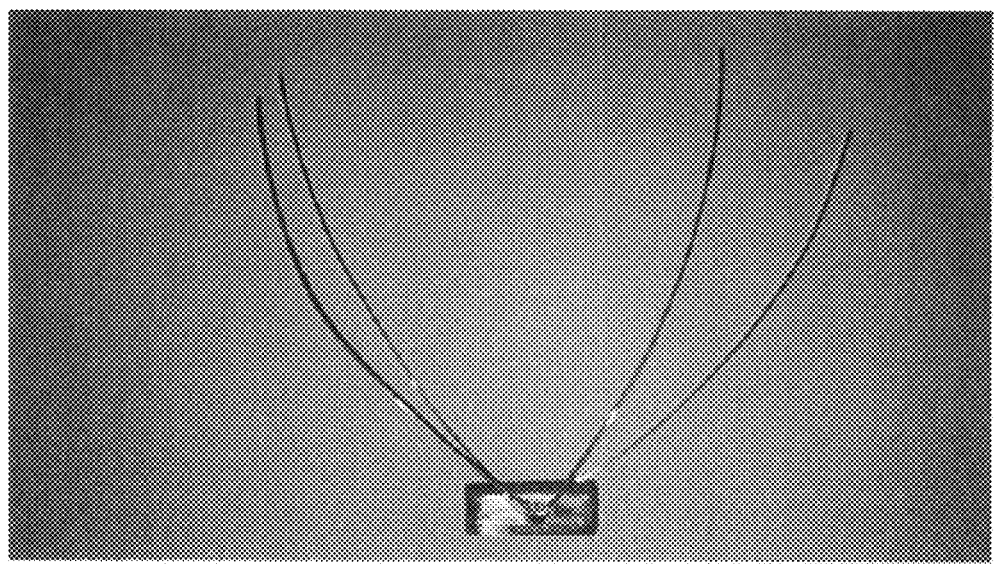
FIG. 5 is a photograph showing a polished surface of a AgCl/AgI/Ag specimen connected with Ag wires according to an embodiment of the present invention.

FIGS. 4 and 5 are photographs showing the specimen connected with Ag wires to evaluate the sensor element for detecting HCl gas.

That is, the specimen of FIG. 4 is manufactured by connecting two Ag wires to the AgCl layer plated with AgI and AgCl on the Ag substrate, and the specimen of FIG. 5 is manufactured by polishing one surface of the sensor element plated with AgI and AgCl on the Ag substrate and connecting two Ag wires to the Ag layer.

Figure 6:
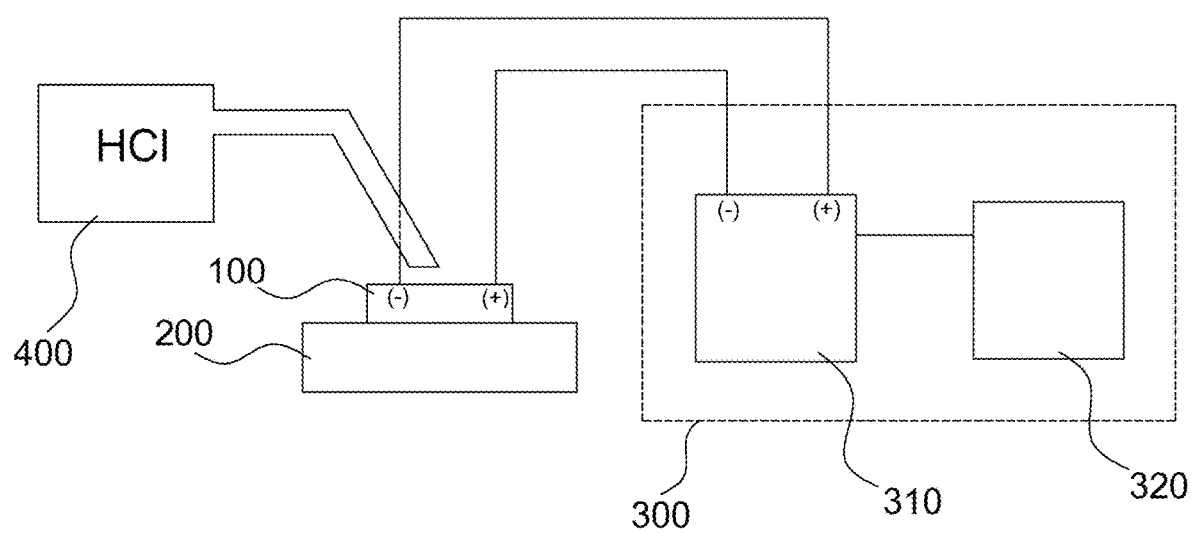
FIG. 6 is a diagram showing a AgCl/AgI/Ag specimen according to an embodiment of the present invention connected to an open circuit voltage (OCV) system.

FIG. 6 shows a sensor element to evaluate a HCl gas sensing property of a AgCl/AgI/Ag sensor element using an open circuit voltage (OCV) measurement system.

The OCV measurement system 300 includes a multi channel potentiostat 310 and a PC for control 320. In addition, the OCV measurement system 300 connects four Ag wires connected to the AgCl/AgI/Ag sensor element 100 to each terminal of the multi channel potentiostat by electric wire. A hot plate 200 is heated and a HCl gas supply device 400 supplies HCl gas. Here, the OCV measurement system 300 measures changes in voltage difference between the plated surface and the polished surface of the AgCl/AgI/Ag sensor element and determines whether the AgCl/AgI/Ag sensor element detects HCl gas.

Figure 7:
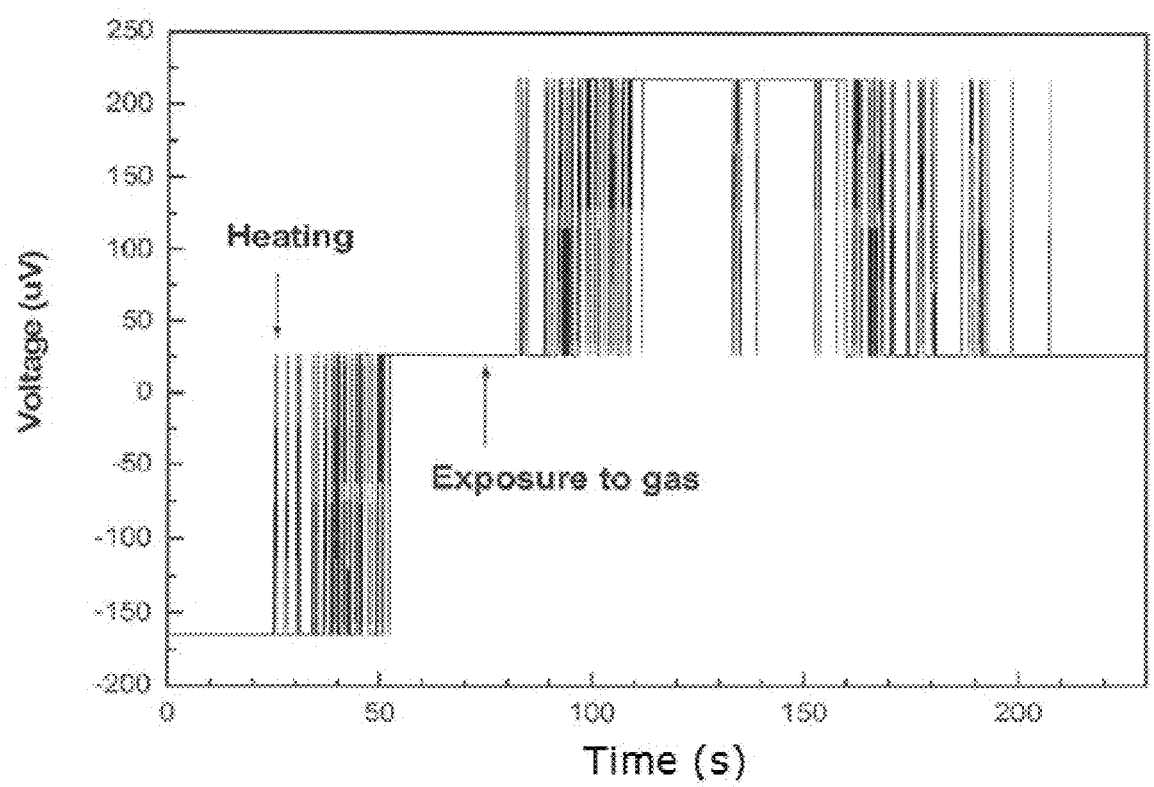
FIG. 7 is a graph showing a change in OCV as a function of time for a AgCl/AgI/Ag specimen according to an embodiment of the present invention.

FIG. 7 shows a result of measuring OCV when supplying HCl gas to the AgCl/AgI/Ag sensor element. The measured result shows that OCV of the sensor element changes by elapsed time.

In detail, first, the AgCl/AgI/Ag sensor element was put on the hot plate and Ag wires connected to the AgCl/AgI/Ag sensor element were connected to the multi channel potentiostat. Next, the sensor element was initially heated by the hot plate after 25 seconds elapsed from start. When the AgCl/AgI/Ag sensor element was heated to an appropriate temperature after 51 seconds elapsed from the start, the OCV was increased by 0.2 mV compared with an initial state. When heating the sensor element, a phase of AgI included in the sensor element underwent a phase transition to a higher conductive phase, so the OCV changed. When HCl gas was supplied to the sensor element after 75 seconds elapsed from the start, the OCV was further increased by 0.2 mV after about 85 seconds elapsed from the start. While HCl gas was supplied constantly, the OCV was maintained at about 0.2 mV. However, the OCV was decreased after 200 seconds elapsed from the start at which supply of HCl gas was blocked. Such results show that $Cl_2$ gas generated from HCl gas supplied to the AgCl/AgI/Ag sensor element reacted with AgCl, which is a sensing material in the sensor element, and the electromotive force changed.

Therefore, the sensor element for detecting HCl gas of the present invention shows a property that the electromotive force thereof changes due to reaction with HCl gas. It is thus possible that the sensor element, which has sensing properties responding to concentration of HCl gas sensitively, may be commercially manufactured by optimizing the function of the element based on such properties.

Next, a manufacturing method of the sensor element for detecting HCl gas according to an embodiment of the present invention will be described. The manufacturing method of the sensor element for detecting HCl gas includes pretreating an ionic layer including a Ag ion, forming an ion conductive layer and a reactive layer on the ionic layer sequentially, and heat treating a sensor element provided with the ion conductive layer and the reactive layer formed on the ionic layer.

At the pretreating step, the Ag substrate is cut to an appropriate size using a cutting machine, polished with sandpaper, ultrasonically cleaned in a solution of trichloroethylene, acetone, and ethyl alcohol for 15 minutes, and dried.

Forming the ion conductive layer and the reactive layer on the ionic layer sequentially is performed by one method or two or more methods selected from the group consisting of plating, depositing, and dipping the Ag substrate pretreated with such a process to laminate a AgI layer and a AgCl layer.

An electroplating method was used for the present invention and will be described. However, various methods can be used for the present invention in addition to the electroplating method.

The electroplating method is a process that coats a surface of a substrate with a different type of material through electrolysis. A basic principle of the plating is electrodeposition by electrolysis and basic elements of the plating process are an anode, a cathode, and an electrolyte. In plating process, the substrate to be plated immersed in an electrolyte including metal ions or metal complex ions and connected to the cathode, which is negative electrode. Metal ions are reduced at the cathode and plated as metal, meanwhile, metal is dissolved at the anode, which is positive metal electrode, by electrolysis, thereby maintaining concentration of metal ions of the electrolyte.

It is important to control a composition of an electrolyte solution, temperature, agitation condition, and current density appropriately so as to obtain a plated layer having a uniform thickness and a high density. An organic additive (polishing agent) that is easy to adsorb on a surface can be added to the electrolyte solution to smooth the surface or to form a uniform plated layer in a curved shape. Such organic additives include pH buffering agents, ligands, surfactants, and thiourea. In order to improve the quality of the plated layer, alternating current or pulses may be applied in addition to direct current.

First, a method of forming the AgI layer on the Ag substrate using the electroplating method will be described. The pretreated Ag substrate was partially immersed in a beaker containing an electrolyte KI solution. In addition, an aluminum plate was immersed to face the Ag substrate in the beaker. Then, a positive electrode of a rectifier was connected to the Ag substrate and a negative electrode of the rectifier was connected to the aluminum plate. Thereafter, a voltage was applied in a constant voltage (CV) mode to perform electroplating of AgI on the Ag plate. In addition, the AgI/Ag specimen was dried using the hot plate to improve an adhesion of the AgI layer to the Ag substrate. At this time, the shape of the AgI layer formed on the Ag substrate can be variously changed by changing the concentration of the electrolyte solution, the voltage, and the plating time.

Next, a method of forming the AgCl layer on the AgI/Ag specimen using the electroplating method will be described.

The AgI/Ag specimen was partially immersed in a beaker containing a KCl solution. In addition, an aluminum plate was immersed to face the AgI/Ag specimen in the beaker. Then, a positive electrode of a rectifier was connected to the AgI/Ag specimen and a negative electrode of the rectifier was connected to the aluminum plate. Thereafter, a voltage was applied in a constant voltage (CV) mode to perform electroplating of AgCl on the AgI/Ag specimen, thereby obtaining the AgCl/AgI/Ag sensor element. In addition, the AgCl/AgI/Ag sensor element was dried using the hot plate to improve an adhesion of the AgCl layer to the AgI layer. Like the AgI electroplating, the AgCl layer is affected by the concentration of the electrolyte solution, the voltage, and the plating time. As shown in FIG. 3, the AgCl/AgI/Ag sensor element manufactured by such methods is signaled by dark purplish coloration since the AgCl layer is disposed atop.

Thereafter, the electroplated AgCl/AgI/Ag sensor element was heat treated. In detail, a surface of the AgCl/AgI/Ag sensor element was polished with sandpaper and the Ag wires were connected to the plated surface and the polished surface using a Ag paste. Two Ag wires were connected to the plated surface and two Ag wires were connected to the polished surface, then manufacturing the sensor element is completed. The sensor element was heat treated to evaporate solvent existing in the Ag paste and then final heat treated in an electric furnace to enhance mechanical stability of the sensor element was performed.

The present invention provides a technique for detecting HCl gas as an element technology for evaluating thermal stability of organic compounds. The sensor element was manufactured with Ag-based solid electrolyte as a main material. The mechanical stability of the sensor element is greatly affected by temperature and time of heat treatment. In addition, the sensor element with four terminals was manufactured, wherein the HCl gas sensing property of the element is capable of being evaluated with the multi channel potentiostat. As a result of measuring the OCV of the sensor element by the supply of HCl gas, the sensor element showed the characteristic of changing the electromotive force in response to HCl gas. Consequently, based on the result of the study, the proposed sensor element structure is suitable for HCl gas sensing and it is possible to commercialize a solid electrolyte based sensor element, which has sensing property that changes sensitively to HCl gas concentration based on the completed prototype element.

DESCRIPTION OF THE REFERENCE NUMERALS IN THE DRAWINGS

100: sensor element for detecting HCl gas
200: hot plate
300: OCV system
310: multi channel potentiostat
320: PC for control
400: HCl gas supply element

What is claimed is:

1. A sensor element for detecting hydrogen chloride (HCl) gas, the sensor element comprising:
    an ionic layer including a Ag ion obtained through ionization;
    an ion conductive layer comprising AgI that is a solid electrolyte, in which the Ag ion is conducted, the ion conductive layer being formed on the ionic layer; and
    a reactive layer comprising AgCl that reacts with the HCl gas, in which the Ag ion conducted from the ion conductive layer and HCl gas react with each other, the reactive layer being formed on the ion conductive layer.

2. A sensor device for detecting HCl gas, the sensor device comprising the sensor element of claim 1.

3. A method of manufacturing the sensor element for detecting HCl gas according to claim 1, the method comprising:
    pretreating an ionic layer including a Ag ion;
    forming the ion conductive layer and the reactive layer on the ionic layer sequentially; and
    heat treating the sensor element provided with the ion conductive layer and the reactive layer formed on the ionic layer.

4. The method of claim 3, wherein the forming the ion conductive layer and the reactive layer on the ionic layer sequentially is performed by any one method or two or more methods selected from the group consisting of electroplating, depositing, and dipping.

* * * * *